US006841032B2

(12) United States Patent
Ikuhara et al.

(10) Patent No.: US 6,841,032 B2
(45) Date of Patent: Jan. 11, 2005

(54) PLASMA PROCESSING APPARATUS FOR ADJUSTING PLASMA PROCESSING THROUGH DETECTING PLASMA PROCESSING STATE WITHIN CHAMBER (75) Inventors: Shoji Ikuhara, Hikari (JP); Junichi Tanaka, Tsuchiura (JP); Hideyuki Yamamoto, Kudamatsu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 47 days.

(21) Appl. No.: 10/094,714

(22) Filed: Mar. 12, 2002

(65) Prior Publication Data
US 2003/0173028 A1 Sep. 18, 2003

(51) Int. Cl.[7] .............................. H05H 1/00; C23C 16/00
(52) U.S. Cl. .............................. 156/345.24; 156/345.25; 118/712
(58) Field of Search ........................ 156/345.24, 345.25; 118/712; 438/5, 8, 14; 216/60

(56) References Cited

U.S. PATENT DOCUMENTS 5,958,258 A * 9/1999 Ishihara et al. ............... 216/60
6,090,302 A * 7/2000 Smith et al. .................. 216/60
6,306,669 B1 * 10/2001 Yano et al. ................... 438/14
6,368,975 B1 * 4/2002 Balasubramhanya et al. .... 438/706
6,383,402 B1 * 5/2002 Smith et al. .................. 216/60
6,521,080 B2 * 2/2003 Balasubramhanya et al. .... 156/345.24
2003/0085198 A1 * 5/2003 Yi et al. ....................... 216/60

FOREIGN PATENT DOCUMENTS

JP    A-2001-60585    3/2001
JP    A-2002-5837     1/2002

* cited by examiner

Primary Examiner—Parviz Hassanzadeh
(74) Attorney, Agent, or Firm—Antonelli, Terry, Stout & Kraus, LLP (57) ABSTRACT A plasma processing apparatus for processing an object arranged within a chamber by utilizing the plasma caused within the chamber, the apparatus including: a sensor having plural lines of a plurality of elements for detecting a plurality of strip-like beams; an application unit for applying the plurality of strip-like beams generated from the light within the chamber in such a way that each of the illumination faces of the strip-like beams makes an angle with respect to each of the lines of the elements; and a control unit for adjusting the operation of the apparatus using outputs from the sensor.

4 Claims, 11 Drawing Sheets

INTENSITY OF INCIDENT BEAM =
100% OF SATURATED INTENSITY OF CCD

|  | COLUMN 1 | COLUMN 2 | COLUMN 3 | COLUMN 4 | COLUMN 5 | COLUMN 6 | TOTAL | TRUE VALUE | ERROR |
|---|---|---|---|---|---|---|---|---|---|
| ROW 1 | 0 | 1 | 2 | 3 | 4 | 5 | 60 | 60 | 0% |
| ROW 2 | 10 | 9 | 8 | 7 | 6 | 5 | | | |

| ERROR OF REFERENCE EXAMPLE |
|---|
| 0% |

(OUTPUT OF EACH PIXEL IS DECIDED AS 10 IN MAXIMUM VALUE)

FIG.8B

INTENSITY OF INCIDENT BEAM =
110% OF SATURATED INTENSITY OF CCD

|  | COLUMN 1 | COLUMN 2 | COLUMN 3 | COLUMN 4 | COLUMN 5 | COLUMN 6 | TOTAL | TRUE VALUE | ERROR |
|---|---|---|---|---|---|---|---|---|---|
| ROW 1 | 0 | 1.1 | 2.2 | 3.3 | 4.4 | 5.5 | 65 | 66 | 1.52% |
| ROW 2 | 10 | 9.9 | 8.8 | 7.7 | 6.6 | 5.5 | | | |

| ERROR OF REFERENCE EXAMPLE |
|---|
| 10% |

FIG.8C

INTENSITY OF INCIDENT BEAM =
120% OF SATURATED INTENSITY OF CCD

|  | COLUMN 1 | COLUMN 2 | COLUMN 3 | COLUMN 4 | COLUMN 5 | COLUMN 6 | TOTAL | TRUE VALUE | ERROR |
|---|---|---|---|---|---|---|---|---|---|
| ROW 1 | 0 | 1.2 | 2.4 | 3.6 | 4.8 | 6.0 | 69.2 | 72 | 3.89% |
| ROW 2 | 10 | 9.6 | 8.4 | 7.2 | 6.0 | | | | |

| ERROR OF REFERENCE EXAMPLE |
|---|
| 20% |

FIG.8D

INTENSITY OF INCIDENT BEAM =
130% OF SATURATED INTENSITY OF CCD

|  | COLUMN 1 | COLUMN 2 | COLUMN 3 | COLUMN 4 | COLUMN 5 | COLUMN 6 | TOTAL | TRUE VALUE | ERROR |
|---|---|---|---|---|---|---|---|---|---|
| ROW 1 | 0 | 1.4 | 2.8 | 4.2 | 5.6 | 7.0 | 76.2 | 84 | 9.29% |
| ROW 2 | 10 | 10 | 9.8 | 8.4 | 7.0 | | | | |

| ERROR OF REFERENCE EXAMPLE |
|---|
| 40% |

PLASMA PROCESSING APPARATUS FOR ADJUSTING PLASMA PROCESSING THROUGH DETECTING PLASMA PROCESSING STATE WITHIN CHAMBER

BACKGROUND OF THE INVENTION

1. Field of the Invention

The present invention relates in general to a plasma processing apparatus including a plasma generation mechanism, and more particularly to a plasma processing apparatus, such as a semiconductor manufacturing apparatus, which is suitable for the fine patterning of semiconductor devices.

2. Description of the Related Art

The fine patterning of the processing for semiconductor devices has made progress year by year, and as a result, the requirement for the size accuracy in the processing has been made more rigorous. On the other hand, in a plasma processing apparatus for generating the plasma operating on the process gases to process physically, chemically an object such as a semiconductor wafer, the reaction products generated in the inside of an apparatus chamber may adhere to the inner wall of the plasma chamber of the apparatus to remain thereon in some cases. Such reaction products within the chamber (vessel) change frequently the conditions of the processing for a wafer as an object of the processing. For this reason, as the processing for a wafer is repeatedly carried out any number of times, the conditions within the apparatus chamber exerting an influence on the processing are changed though the setting for the apparatus is held fixed, and as a result, the shape of the surface of the processed wafer, or the like is changed from the initial shape. Thus, there arises the problem that it is impossible to produce stably the objective semiconductor devices or the like.

In order to cope with the above-mentioned problem, there has been taken the measures in which the deposited materials on the inner wall of the chamber are removed by utilizing the plasma (cleaning), the temperature of the chamber wall is adjusted in order to make the deposited materials hardly adhere to the chamber wall, and so forth. However, the above-mentioned process conditions are changed until the removal of the deposited materials, and in addition thereto, it is difficult to remove the deposited materials to reduce sufficiently the change in state of the processing for wafers.

For this reason, the conditions of the apparatus and the processing state when the wafers are processed are gradually continued to be changed, and hence it is required for a user of the apparatus that the change in conditions of the apparatus and in processing state is detected before the change in processed shape has become the serious problem for the manufacture of the products, and then the plasma processing apparatus is decomposed to carry out the exchange of the parts and the cleaning using suitable liquid or a supersonic wave.

Furthermore, in addition to such deposited films adhering to the inside of the apparatus chamber, the fluctuation of the various factors such as the temperatures of the processing system takes part in the cause by which the apparatus conditions for the processing of wafers and the processing state fluctuate. In order to solve such a problem, there has been taken the measures of detecting the change in processing state in the inside of the plasma processing apparatus to carry out the cleaning depending on the detection result, or there has been made the device of feeding the detection result back to an input of the plasma processing apparatus to hold the processing state fixed.

One example of such a prior art is disclosed in JP-A-2001-60585 (prior art 1). This prior art 1 relates to a plasma etching apparatus which is designed in such a way that the electromagnetic radiation from the plasma within a chamber is measured through view ports formed in a sidewall, a top portion and a bottom portion of the chamber for the etching to transmit the measurement result to a process monitoring apparatus having a spectrometer and a processor through a fiber cable and the like. The process gases, the reaction products and a plurality of other plasmas are contained in the plasma within the chamber, and the electromagnetic radiation (luminous radiation) from the plasma within the chamber is measured by the spectrometer of the process monitoring apparatus to split the light from the plasma into a plurality of beams having different wavelengths which are in turn supplied to an array of a silicon charge coupled device. Then, it is possible to calculate the intensity of beam for each of the wavelengths using the outputs from the charged coupled device by the processor. As a result, it is possible to detect the information of the intensities of plural plasmas contained in the electromagnetic radiation. The above-mentioned contents are disclosed in the prior art 1.

In addition, the technique for detecting a plurality of beams having different wavelengths from such luminous radiation from the plasma within the chamber to analyze them is disclosed in JP-A-2002-5837 (prior art 2). The prior art 2 is such that it includes an optical detector having a plurality of charge coupled devices (CCDs) for subjecting the light from the plasma flame into the spectrum processing to obtain a plurality of beams having different wavelengths using a diffraction grating to detect a plurality of beams thus obtained after the spectrum processing, and the images of the beams having the different wavelengths are respectively imaged on the CCDs to analyze the quantities of elements, in the measurement components, differing in wavelength from one another using the intensities of the beams measured in the respective devices of the optical detector.

SUMMARY OF THE INVENTION

The above-mentioned prior arts 1 and 2 have the following problems.

That is, in the above-mentioned prior arts, in response to the beams which have been obtained after the spectrum processing in the detection means such as CCDs, the information of the beams is detected. However, the point that the accuracy when detecting the rays of light, of the plasma, having a plurality of wavelengths corresponding to a plurality of reactions as the subject of the detection is enhanced, or the detection quantity is increased while reducing an error is not taken into consideration at all.

As described above, in the plasma processing apparatus, the rays of light due to the phenomena such as a plurality of reactions, the bonding of the products, and the decomposition are contained in the plasma within the apparatus chamber, and the rays of light emit the beams having peculiar wavelengths. Therefore, the rays of light having peculiar wavelengths are detected, whereby it is possible to grasp precisely the phenomena generated within the apparatus chamber. In other words, these wavelengths correspond to the reactions generated in the chamber, the intensity or quantity of plasma, the quantities of products, the kind of products, and the like. Then, if the intensities of spectra having these wavelengths (the quantities such as the intensities of the rays of light) are detected, then it is possible to determine the apparatus state using the change in time or the absolute quantities for example.

On the other hand, for the purpose of adjusting the running of the apparatus, it is necessary to grasp a plurality of reactions and the phenomena. For this reason, it is required to detect the rays of light having a plurality of wavelengths to grasp them. For example, the intensities of generated rays of light have large and small peaks in the range of the detected wavelengths, and these peaks may be important irrespective of the intensities thereof (the magnitude of the peak values) in some cases. Some of the rays of light important for the evaluation and judgement of the state, though the generation intensities or the quantities of products are small, are contained in the reactions or the processing within the chamber. Therefore, it is necessary to detect even the data of the wavelengths each having a small peak with higher accuracy in terms of carrying out such evaluation and judgement with high accuracy.

For the purpose of enhancing the accuracy with which the data of such wavelengths each having a small peak is detected, it is conceivable to increase the quantity of data outputted from the detection sensor. However, if the sensitivity of the detection sensor is only increased or the quantities of beams applied to the sensor is merely increased, the data of the wavelengths each having a large peak is correspondingly increased. As a result, there is the possibility that the quantity of beam detected by the element on the sensor, such as a CCD, for detecting the beam with a wavelength having a large peak may be saturated. If the quantity of beam detected by an element is saturated, then it is impossible to increase the quantity of beam up to the level equal to or larger than the saturated quantity, or to enhance the sensitivity of the sensor. As a result, the difference between the quantity of actual beam and the detection quantity is increased, and hence there arises the problem that an error in the measurement or detection is increased.

If an error in detection and measurement is increased, then it is impossible to determine accurately the processing state, and hence it becomes impossible to carry out precisely the processing. As a result, the precise processing can not be carried out for the object such as a semiconductor wafer, and also the yield of the processing is reduced to increase the manufacturing cost.

The above-mentioned problems are not taken into consideration in the prior art.

In the light of the foregoing, the present invention has been made in order to solve the above-mentioned problems associated with the prior art, and it is therefore an object of the present invention to provide a plasma processing apparatus which is capable of carrying out the processing more precisely.

In order to attain the above-mentioned object, according to one aspect of the present invention, there is provided a plasma processing apparatus for processing an object arranged within a chamber by utilizing the plasma caused within the chamber, the apparatus including: a sensor having plural lines of a plurality of elements for detecting a plurality of strip-like beams; an application unit for applying the plurality of strip-like beams generated from the light within the chamber in such a way that each of the illumination faces of the strip-like beams makes an angle with respect to each of the lines of the elements; and a control unit for adjusting the operation of the apparatus using outputs from the sensor.

In addition, according to another aspect of the present invention, there is provided a plasma processing apparatus including: a sample stage, arranged within a chamber, for placing thereon an object to be processed; a plasma generation unit for generating the plasma within the chamber; a spectroscope for introducing thereinto the light within the chamber through a slit to generate a plurality of beams having different wavelengths; a sensor having a plurality of elements, disposed in a plurality of predetermined lines, for detecting the beams; a detector for detecting the intensities of the plurality of beams using outputs from the sensor; and a controller for adjusting the processing for the object to be processed using outputs from the detector, wherein the plurality of beams are applied onto the elements in such a way that each of the illumination faces of the beams on the surface of the sensor makes an angle with respect to each of the lines of the elements.

Other objects, features and advantages of the invention will become apparent from the following description of the embodiments of the invention taken in conjunction with the accompanying drawings.

DESCRIPTION OF THE EMBODIMENT

The embodiment of the present invention will hereinafter be described in detail with reference to the accompanying drawings.

Figure 1:
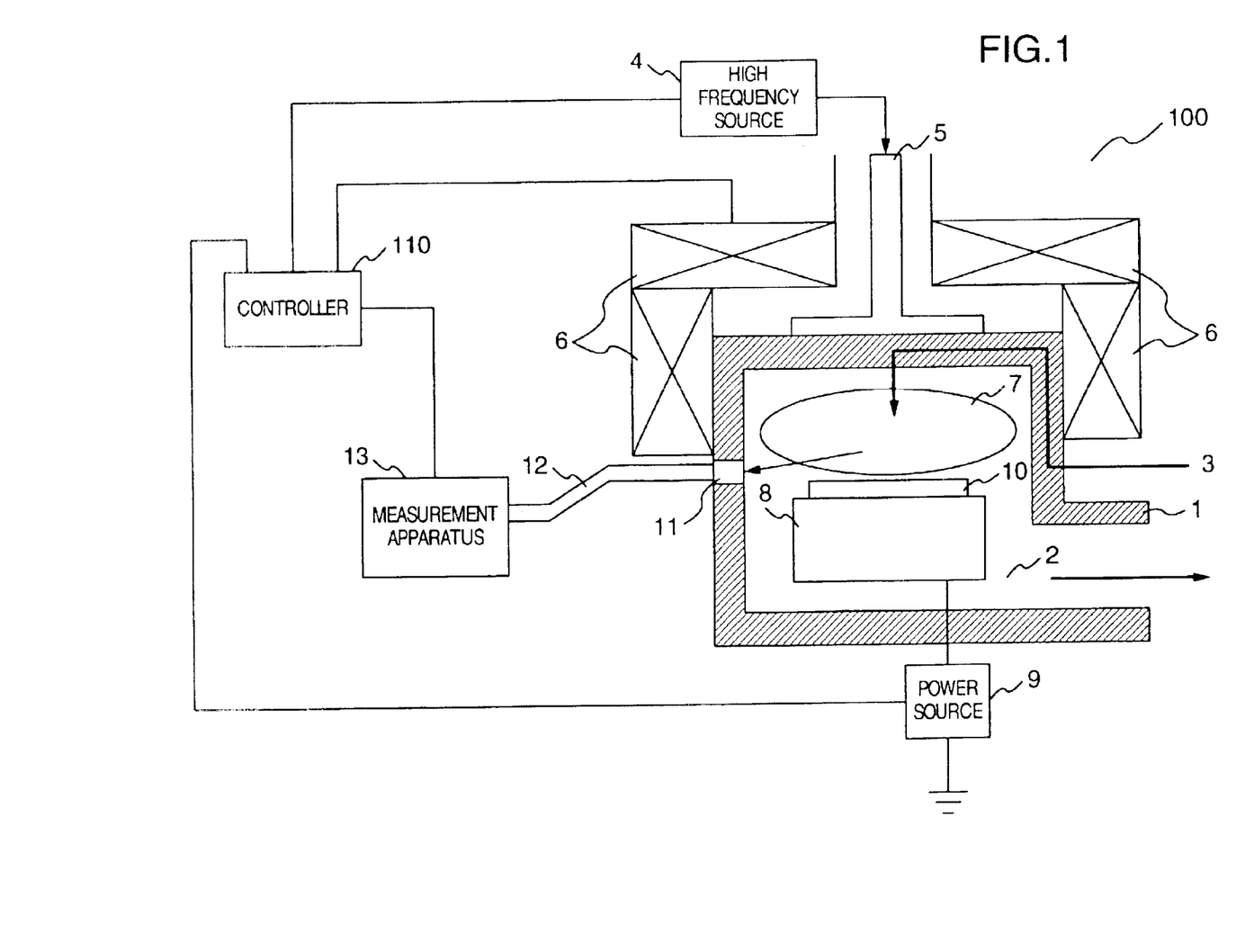
FIG. 1 is a cross sectional view showing the outline of a plasma processing apparatus according to an embodiment of the present invention.

FIG. 1 is a cross sectional view showing schematically construction of a plasma processing apparatus according to an embodiment of the present invention. The main body of a plasma processing apparatus 100 of the present embodiment includes a processing vessel (a processing chamber or a chamber) 1, a sample stage 8 which is disposed in the inside of the processing chamber 1 and on which a sample 10 is placed, and exhaust means (not shown) for exhausting gases within the chamber 1 through an exhaust port 2. Process gases 3 are supplied into the chamber 1 to generate the plasma in the inside of the chamber 1 and above the sample stage 8 and the sample 10, and the surface of the sample 10 is subjected to the processing such as the etching or the impurity removal therefrom by utilizing the plasma. As for the sample 10, in the present embodiment, there is conceivable a wafer becoming a substrate of a semiconductor device such as a semiconductor memory, a computing element or a magnetic head device. In the periphery of the above-mentioned chamber 1, there are provided a high frequency source 4, such as a magnetron, for supplying a high frequency electromagnetic wave to the inside of the chamber 1, an antenna 5 for in response to the high frequency electromagnetic wave supplied from the high frequency source 4, controlling the propagation of the high frequency electromagnetic wave in such a way that it is propagated throughout the inside of the whole chamber 1 and above the sample 10, and magnetic field generation means 6 for forming the magnetic field in the space within the chamber 1 and above the sample stage 8. In addition, apparatus measurement means (not shown) for detecting the processing state of the sample 10 and the state of the plasma caused for the processing in the inside of the chamber 1 is mounted to the apparatus 100. Also, in order to lead the particles (ions, radicals or the like), the electrons and the like for the processing which are generated through the plasma by applying a suitable voltage onto the sample 10 placed on the sample stage 8 onto the surface of the sample to make them incident thereto, a high frequency voltage is applied from a power source 9 to the sample 10 and the sample stage 8. One end side of the power source 9 for supplying the high frequency voltage is grounded and the other end side thereof is connected to the sample stage 8.

In addition, a window 11 through which the inside of the chamber 1 is measured using an optical fiber 12 is formed in the sidewall of the above-mentioned chamber 1, and the optical fiber 12 is connected to a measurement apparatus 13. The measurement apparatus 13 is adapted to detect the state of the processing carried out in the chamber and the state of the apparatus, e.g., the speed of the progress of the processing and the kind of processing, the kind of generated products and the quantity of generated products adhered to the inside of the chamber, and the like to generate the information required to determine the advisability of discontinuance and continuance of the processing, a time point of completion of the processing, and the like.

Furthermore, in the present embodiment, the plasma processing apparatus 100 includes a controller 110 for in response to an output from the measurement apparatus 13, adjusting the running of the apparatus 100. The controller 110 is adapted to detect and calculate the conditions in the chamber, the running conditions of the apparatus 100 for the advisability of discontinuance and continuance of the above-mentioned processing, and the processing itself to issue instructions to the high frequency source 4, the antenna 5, the electromagnetic generation unit 6, the high frequency power source 9 and the exhaust means (not shown) or to issue an instruction for the gas supply, thereby carrying out the adjustment required for the running of the apparatus 100. Moreover, it is also possible to provide a user of the apparatus with the information of the conditions of the running, the discontinuance and continuance of the processing, and completion of the processing.

Figure 2:
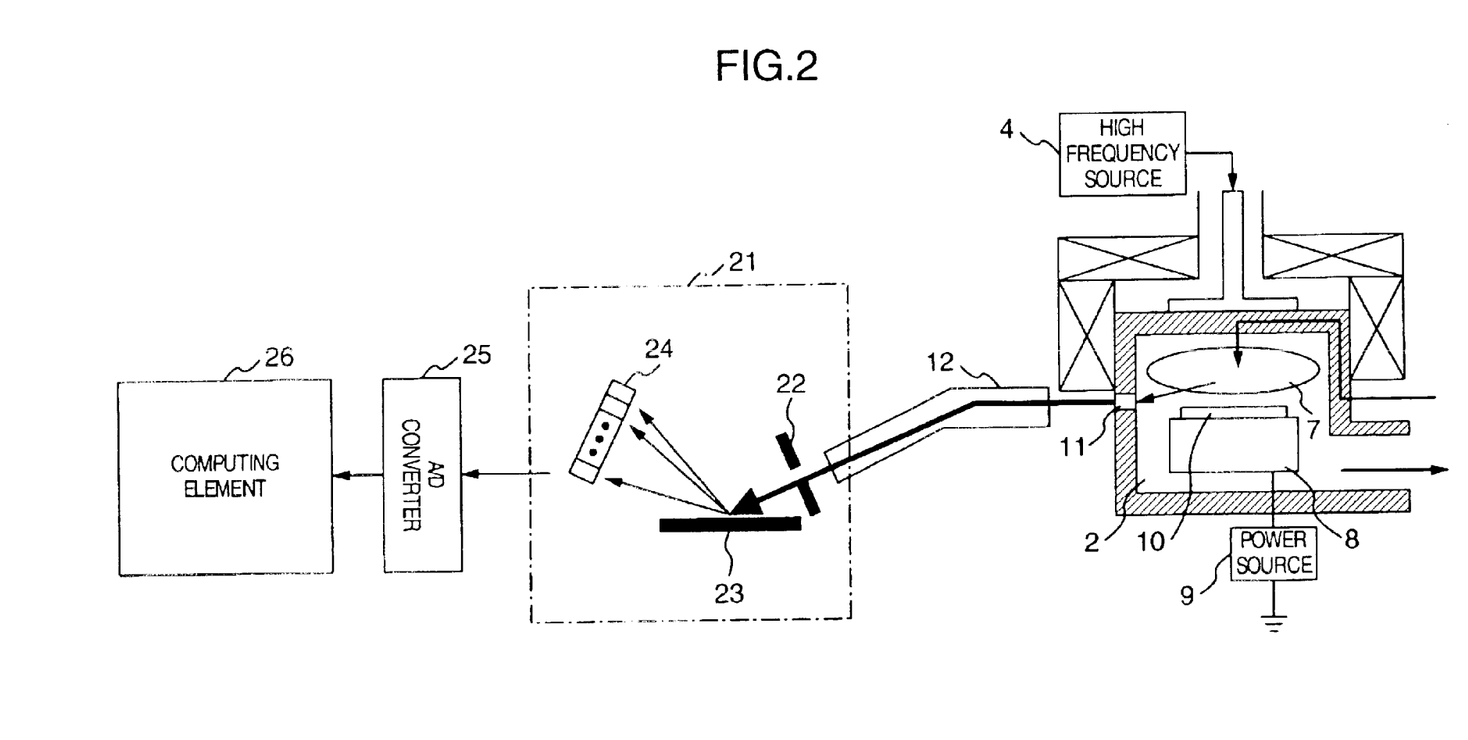
FIG. 2 is a schematic view, partly in cross sectional view, useful in explaining the construction for the detection of beams of the present embodiment shown in FIG. 1.

In the above-mentioned measurement apparatus 13, the inside of the chamber 1 is measured through the window 11 to detect the light within the chamber. The construction for the detection of light will now be described in more detail with reference to FIG. 2. FIG. 2 is a schematic diagram useful in explaining the construction for the light detection in the present embodiment shown in FIG. 1. The light within the chamber generated due to the plasma or reactions in the plasma in the present embodiment contains the light emitted from the background, the noise and the like which are detected together with that light. The light within the chamber 1 is transmitted to the measurement apparatus 13 through the optical fiber 12 via the window 11 formed in the sidewall of the chamber 1 and then is split every wavelength within the measurement apparatus 13 to measure the intensities of the resultant beams, thereby detecting the state of the above-mentioned processing and the state of the apparatus. In the present embodiment, the light is subjected to the spectrum processing by the well known means such as a spectroscope 21 to be detected thereby. In the spectroscope 21, the introduced light is condensed through a slit 22 so that the resultant light having a strip-like shape in cross section is introduced into a diffraction grating 23. Then, the introduced strip-like light is split into beams, contained therein, every different wavelength to be outputted. That is, each of the beams having the different wavelengths after having been subjected to the spectrum processing has the strip-like shape in which the illumination face thereof in application onto an arbitrary surface has a predetermined width and a predetermined length. These beams are outputted in the form of a plurality of strip-like beams.

The beams having the different wavelengths obtained after the spectrum processing are then measured in a detection sensor 24 for detecting beams. In the present embodiment, the detection sensor 24 is constituted by the so-called CCD, and the intensities of the beams are detected and measured by the individual elements for detection constituting the CCD. In the detection sensor 24, in order to receive a plurality of strip-like beams having the different wavelengths after the spectrum processing, the elements constituting the sensor 24 are disposed into a face-like shape (i.e., in such a way as to form a face), and the elements of the sensor 24 contained in the areas each having an area receive the incident strip-like beams to detect the quantities of strip-like beams, respectively. The strip-like beams which have been detected by the sensor (CCD) 24 are converted into digital data by an A/D converter 25 to be transmitted to a computing element 26. In the computing element 26, the numerical arithmetic operation is carried out using the above-mentioned digital data, and the intensities of the beams detected in the sensor 24 are calculated to be detected.

Figure 3A:
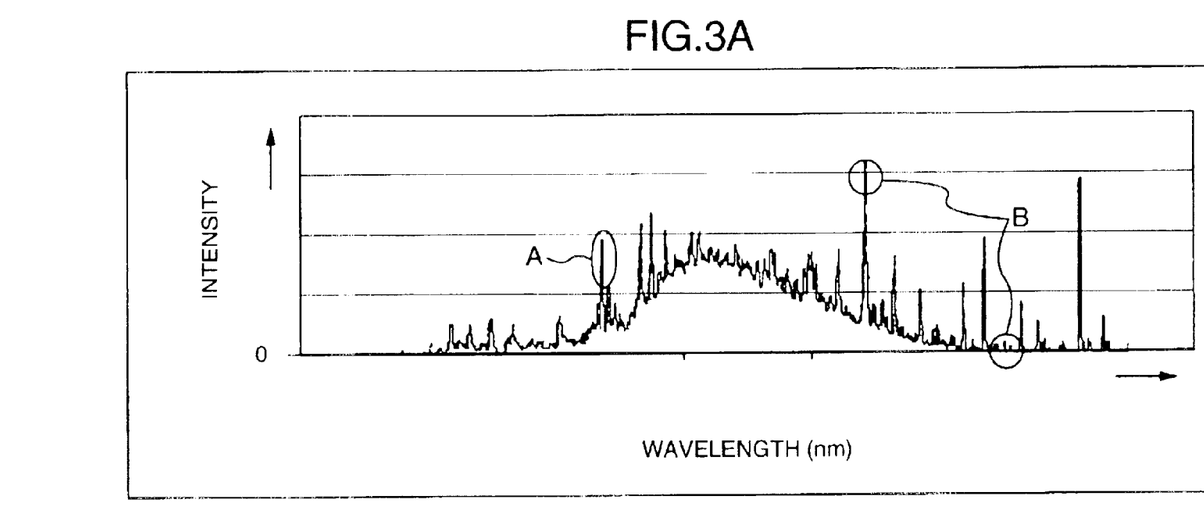
FIGS. 3A and 3B are respectively graphical representations each showing an example of data obtained from the light, within a chamber, which is measured in the present embodiment shown in FIG. 1.
Figure 3B:
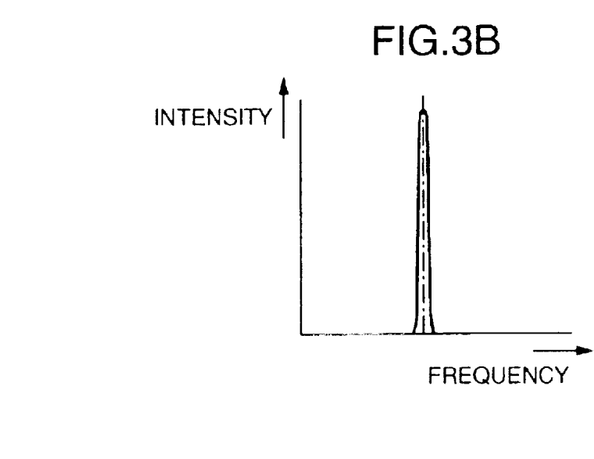

FIGS. 3A and 3B show an example of the data obtained after having subjected the light propagated within the chamber 1 and measured in the present embodiment, e.g., the plasma light to the spectrum processing, i.e., the data of the so-called spectral energy distribution. In the example shown in these figures, it is determined that the beam, as shown in FIG. 3A, has a peak every wavelength of the spectra, and the expense of the output in the left-hand and right-hand sides (the magnitude of the wavelength) of the wavelength having the peak is small and hence the spectrum has a sharp peak as shown in FIG. 3B. The intensities of the generated beams have large and small peaks in the range of the detected wavelengths as shown in A and B of FIG. 3A, and these peaks become important irrespective of the intensities thereof (the magnitudes of the peaks) in some cases. These wavelengths correspond to the reaction caused in the chamber, the intensity and quantity of plasma and quantities and kinds of products. Thus, the intensities of spectra of these wavelengths (quantities such as the intensities of beams) are detected and for example, the change in time or the absolute quantity is used, whereby it is possible to determine the state of the apparatus. Since the important elements for the evaluation and the judgement of the state, though the generation intensities or quantities, or the quantities of products are small, are contained in the reaction or the processing within the chamber, it is necessary for the purpose of carrying out the evaluation and judgement with high accuracy to detect even the data of the wavelengths each having a small peak with higher accuracy.

For the purpose of enhancing the accuracy with which the data of the wavelength having such a small peak, it is conceivable to increase the amount of data outputted from the sensor 24. However, if the sensitivity of the sensor 24 is only increased or the quantities of beams applied to the sensor 24 are merely increased, there is the possibility that the amount of data of the wavelengths each having a large peak may be also increased and hence the quantity of beam detected by the element of the sensor 24 in the area for detection of the beam with the wavelength having a large peak may be saturated. For this reason, there is required the means for enhancing the performance of the detection in the range of a certain peak value to fulfill the predetermined accuracy.

Figure 4A:
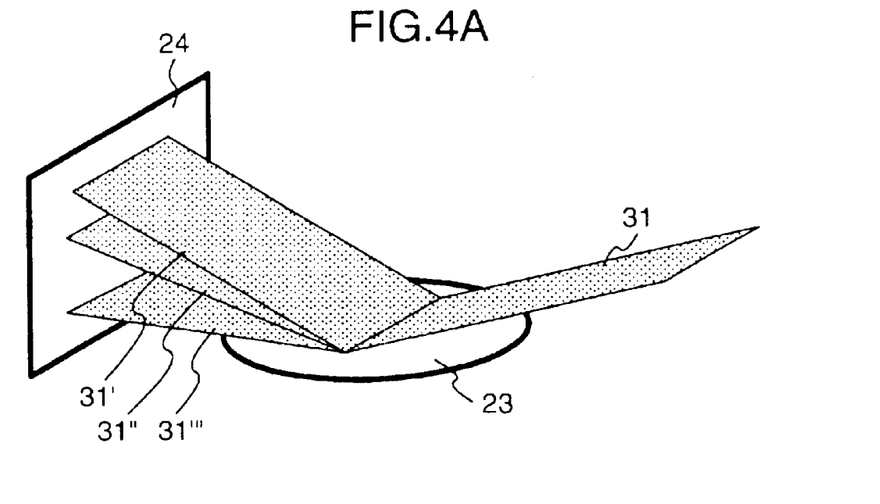
FIGS. 4A and 4B are respectively a perspective view and a schematic view each showing the situation in which the light is subjected to the spectrum processing to be detected in the embodiment shown in FIG. 1.

FIGS. 4A to 8D show the outline of the construction for the measurement of the spectra of the beams in the present embodiment. Then, FIGS. 4A and 4B are respectively schematic views each showing the situation in which the light within the chamber is subjected to the spectrum processing in the spectroscope 21 to be detected. As shown in FIG. 4A, the light which has been introduced into the spectroscope 21 through the fiber 12 is condensed into the strip-like light through the slit 22 having a shape having a predetermined width and a predetermined length, e.g., a long and narrow shape to be made incident to the diffraction grating 23 to be outputted therefrom in the form of the strip-like beams 31', 31", and 31''' into which the original light is split every wavelength. These strip-like beams after the spectrum processing have shapes (long and narrow shapes) into which the illumination faces thereof in application onto the surfaces of the elements of the CCD of the sensor 24 disposed in predetermined lines are influenced by the shape of the slit. These strip-like beams are transmitted to the sensor (CCD) 24 to be made incident to the elements constituting the sensor 24. The elements disposed in the face-like area have the structure having predetermined lines. Then, the quantities of incident strip-like beams can be detected by utilizing this line of the elements.

Figure 4B:
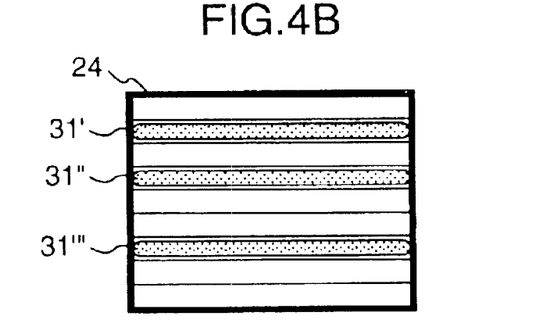

For example, as shown in FIG. 4B, the line of the elements forms the transverse rows on the drawing. Then, when a plurality of rows of the elements are formed, it is conceivable that the strip-like beams 31', 31" and 31''' are applied onto these rows along the rows. As a result, the spectral light having the wavelength of interest is detected using the output for each of the rows of the elements, whereby it is possible to enhance the accuracy of the detection. However, when the sensitivities of the elements are uniformly increased for the purpose of enhancing the accuracy of the measurement and detection as described above, if the quantity of beam detected by one element is saturated so that a quantity of beam equal to or larger than that quantity can not be detected in the one element, then the quantities of beams detected by the elements in the line (row) constituted by the one element of interest are similarly saturated. As a result, the accuracy is reduced with which the beam having the wavelength of interest is detected.

Figure 5:
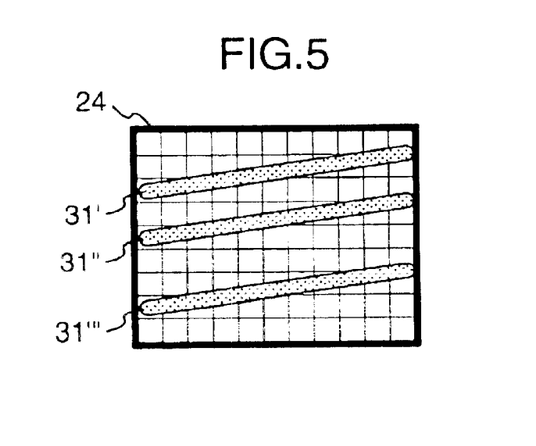
FIG. 5 is a schematic view showing the relationship between a sensor employed in the present embodiment and the strip-like beams after the spectrum processing.

The disposition relationship between the sensor employed in the present embodiment and the beams after the spectrum processing will now be described with reference to FIG. 5. FIG. 5 is a schematic diagram showing the disposition relationship between the sensor employed in the present embodiment and the beams after the spectrum processing. In the present embodiment, as shown in the figure, the direction of the strip-like beams makes an angle with respect to the rows of the elements of the sensor 24. Thus, the spectrum of the beam having one wavelength is detected by the elements of the different rows. As described above, since the strip-like beams after the spectrum processing are made incident to the sensor in such a way as to make an angle with respect to the line of the elements, e.g., the vertical element line (column) and the transverse element line (row) in the figure, the beams are detected by a plurality rows (or columns) of elements.

Figure 6:
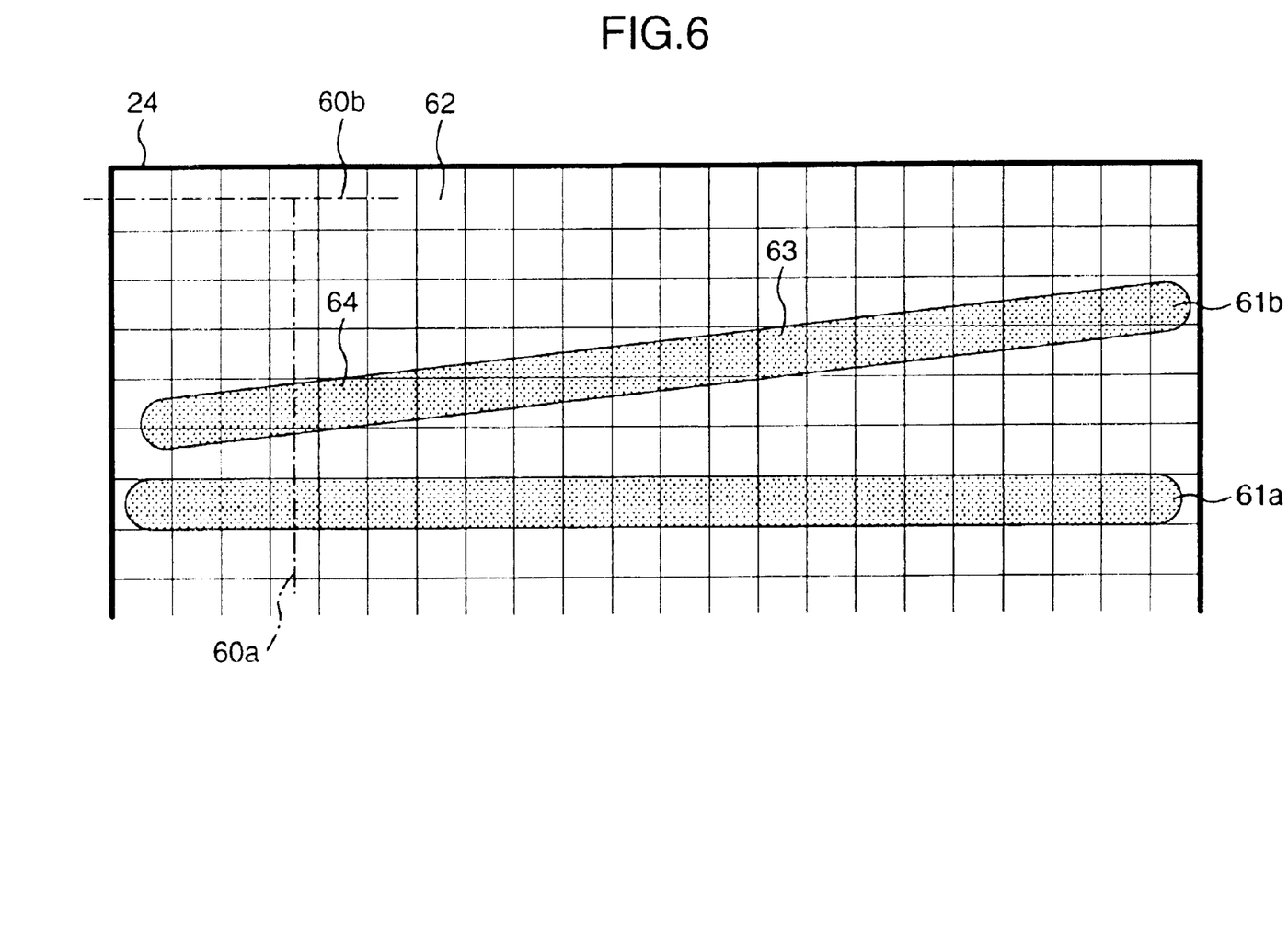
FIG. 6 is a schematic view showing an example of the application of the strip-like beams onto the optical detection sensor in the present embodiment shown in FIG. 1.

An example of the application of the beams to the sensor in the present embodiment will hereinbelow be described in more detail. FIG. 6 is a diagram showing an example of the application of the beams to the optical detection sensor in the present embodiment shown in FIG. 1. The detection sensor 24 is constituted by the CCD in which the elements for detecting the beams are disposed into the lattice-like arrangement so as to be adjacent to one another in the vertical direction and in the transverse direction, and the beams can be detected in the areas each having a predetermined area. In the figure, the structure of this sensor 24 is schematically described. Then, while each part between the adjacent elements in the lattice is illustrated by a line, in actual, the member or the like for insulating electrically the adjacent elements is disposed between the adjacent elements in the lattice and hence a distance is defined between the adjacent elements. In the figure, the elements for detecting the beams are illustrated in such a way as to correspond to lattice elements, and a lattice element 62 represents the photoelectric receiving device provided in the inside of the lattice. These lattice elements 63s are formed in the vertical direction 60a and in the transverse direction 60b, and thus the adjacent elements are disposed into the lattice-like arrangement in these directions. In addition, a strip-like beam 61a which is applied onto the elements along the line (row) in the transverse direction on the drawing is shown as a reference example of the strip-like beam corresponding to an arbitrary wavelength and applied onto the sensor 24. Furthermore, a strip-like beam 61b is shown as an example of the strip-like beam which corresponds to an arbitrary wavelength and which is applied onto the sensor in such a way as to make an angle with respect to the line in the row direction of the elements.

The strip-like beam 61a is applied onto the elements disposed in the row direction. Thus, the quantities of parts of the beam detected by the elements receiving the beams and disposed in this row direction are roughly equal to one another in the elements on this row except for the elements receiving the both ends of the beam and disposed at the both ends of this row. On the other hand, the strip-like beam 61b is applied onto the elements over the lines of a plurality of lattice elements in the vertical direction (the lines of a plurality of rows). In the present embodiment, the quantities of parts of the beams which are respectively detected by lattice elements 63 and 64 are roughly equal to each other.

However, the quantities of parts of the beam which are respectively detected by the lattice elements other than the lattice elements 63 and 64 are different from one another. If we think that the quantities of parts of the beam detected by the elements are increased under this state, then it is conceivable that in the case of the strip-like beam 61*a*, if the quantity of part of the beam detected by one element is saturated, then the quantities of parts of the beam detected by other elements are similarly saturated. Thus, even if the quantities of parts of the strip-like beam received thereby are each increased after the saturation, the quantities of part of the beam detected thereby are not increased, and as a result, an error in the qualities of detected parts of the beam is increased. On the other hand, in the case of the strip-like beam 61*b*, even if the quantities of parts of the beam which are respectively detected by the lattice elements 63 and 64 are saturated, the quantities of parts of the beam which are respectively detected by other lattice elements are not saturated. For this reason, even if the quantities of parts of the beam received by the lattice elements 63 and 64 are further increased, it is possible to detect the quantity of beam, e.g., the intensity of the beam. In addition, since the number of lattice elements in which the quantities of parts of the beam are saturated is small, it is possible to suppress the increase in error.

Figure 7A:
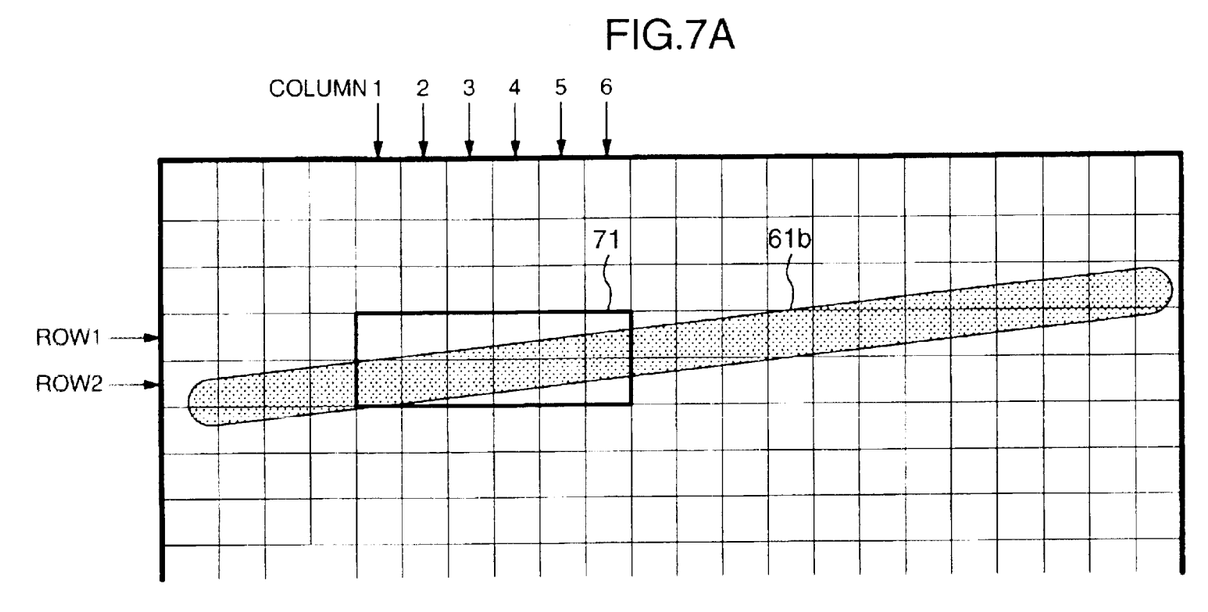
FIGS. 7A and 7B are respectively a schematic view and a diagram each showing beam receiving areas of the elements of the sensor for the application of the strip-like beams in the present embodiment.
Figure 7B:
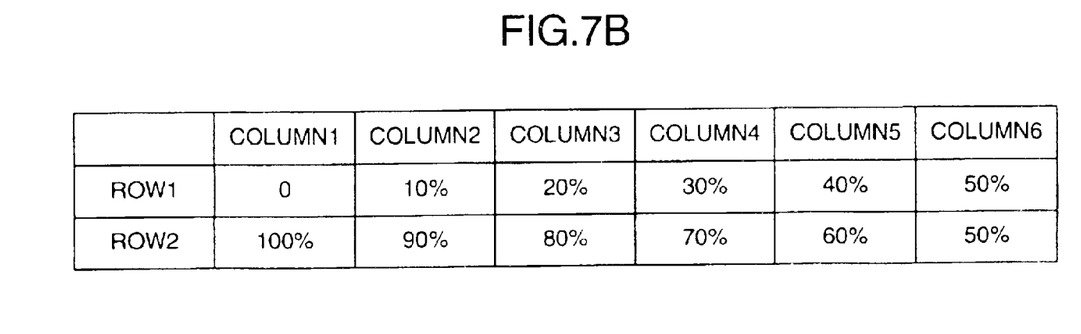

The operation in the present embodiment will hereinbelow be described with reference to FIGS. 7A to 8D. In the description of these figures, since the intensity of the beam detected in each of the lattice elements is generally concerned with the beam receiving area, the intensity of the beam is represented in the form of a numeric value using this beam receiving area. FIGS. 7A and 7B are respectively diagrams each showing the beam receiving areas of the elements of the sensor with respect to the application of the strip-like beam in the present embodiment. As shown in FIG. 7A, in the present embodiment, the strip-like beam is applied in such a way as to make an angle with respect to the direction of the line of the elements of the sensor. FIG. 7B shows the beam receiving areas of the elements in a predetermined range 71 onto which the strip-like beam is applied. In FIG. 7B, there are shown the beam receiving areas of the lattice 71, corresponding to the range having rows 1 and 2 and columns 1 to 6 on the drawing, of the lattice elements onto which the strip-like beam is applied. As shown in the figure, in these twelve lattice elements, the lattice element having the beam receiving area of 100% is only the lattice element located in a row 2 and a column 1, and hence the beam receiving areas of other lattice elements are equal to or smaller than 100%. In other words, with respect to the strip-like beam detected in this area, each of the intensities of parts of the beam detected by other lattice elements is each smaller than the intensity of part of the beam detected by the lattice element in the row 2 and the column 1.

FIGS. 8A to 8D are respectively diagrams each useful in explaining the difference in detection of the beam in the example of the beam application shown in the strip-like beams 61*a* and 61*b* of FIG. 6, and show the effect of the detection of the beam in the present embodiment in the form of numeric values. In those figures as well, similarly to FIG. 7B, the beam receiving areas of the lattice elements are shown as the representation of the quantities (intensities) of parts of the beam detected by the elements of the sensor corresponding to these lattice elements. In those figures, the intensity of the incident beam 61*b* detected in the area 71 is calculated every lattice element. In addition, there are shown the numeric values which are obtained by simulating errors between the detected outputs and the actual intensities of the incident beams when increasing the intensity of the incident beam.

Figure 8A:
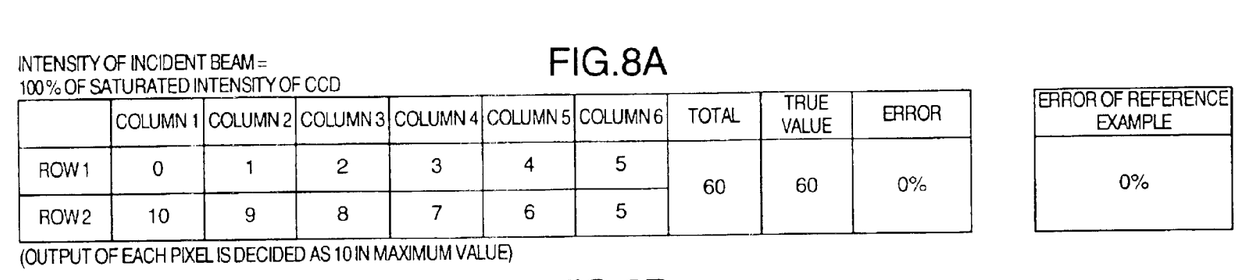
FIGS. 8A to 8D are respectively diagrams each useful in explaining the effect of the beam detection in the present embodiment.
Figure 8B:
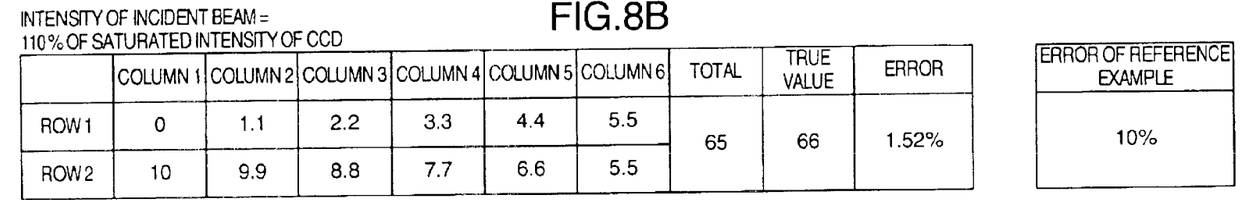
Figure 8C:
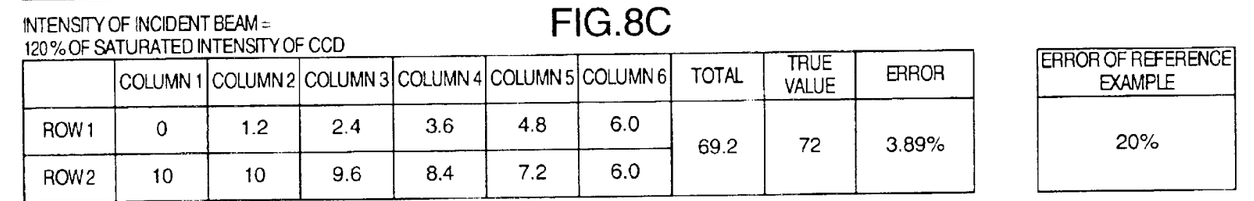
Figure 8D:
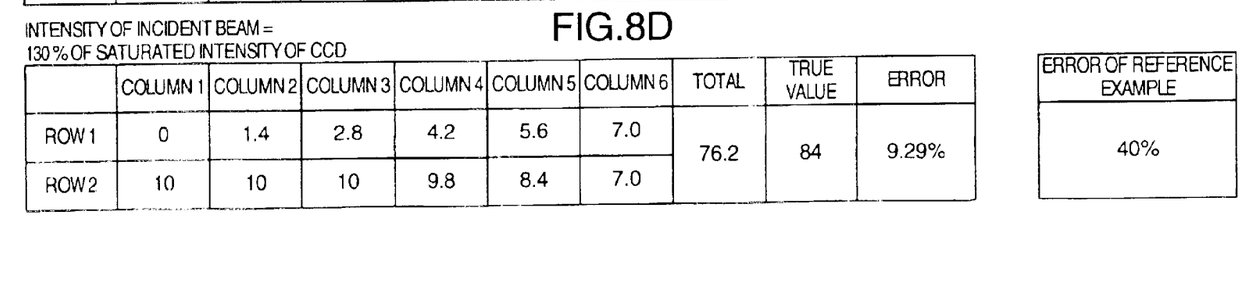

FIG. 8A shows the case where the intensity of the incident beam is 100% of the intensity at which the quantity of beam detected by the element corresponding to the lattice element of interest is saturated. In this case, it is conceivable that the total of the intensities of parts of the beam detected by the elements is equal to the actual value of the intensity of the incident beam. Therefore, as shown in the right-hand end, it is conceivable that there is no error between the present case and a reference example shown in the strip-like beam 61*a* of FIG. 6. On the other hand, FIGS. 8B to 8D show the cases where the intensity of the incident beam is respectively set to 110%, 120% and 140% of the intensity at which the quantity of beam detected by the element corresponding to the lattice element of interest is saturated. If the intensity of the incident beam is increased in such a manner, though the total of the outputs of the intensities of parts of the beam detected by the elements is increased, the number of elements each having the saturated output is also increased. As a result, the difference (error) between the intensity of the incident beam and the actual value is increased. However, as described above, since the number of elements each having the saturated output is small as compared with the reference example 61*a*, the increase in error can be relatively suppressed as compared with the reference example 61*a*. For this reason, it is also possible to enhance the accuracy of the detection by increasing the detection output, while it is also possible to suppress the increase in error. For example, in the case of the plasma processing apparatus for etching, an error which is allowed for the difference in judgement for completion of the processing is about 10%. Then, according to the present embodiment, it is possible to increase the sensitivity by 40%, and hence the error can be remarkably reduced as compared with the reference example.

Figure 9:
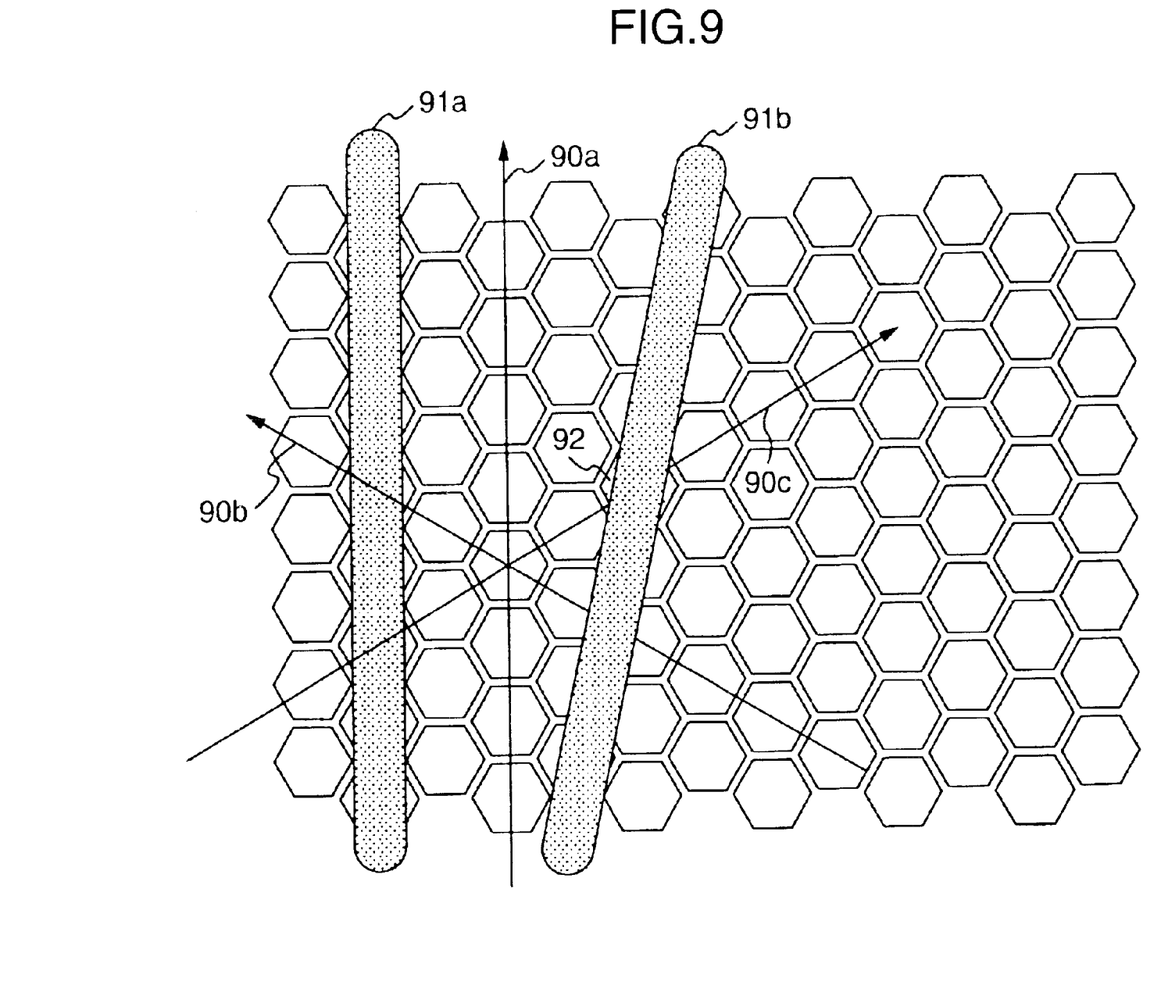
FIG. 9 is a schematic view of a modification, of the present embodiment, showing an example of another disposition of elements.

FIG. 9 is a modification of the above-mentioned embodiment showing an example of another disposition of the elements. In this modification, the direction of the line of the elements is different from the example shown in FIGS. 5, 6 and 7A. That is, the six elements are disposed adjacent to one another in the six directions of the periphery of an arbitrary one element. For this reason, an arbitrary one element has lines 90*a*, 90*b* and 90*c* of the adjacent elements in three directions on the drawing. Reference numerals 91*a* and 91*b* designate respectively examples of the application of the strip-like beams to the lines of the elements of the sensor. That is, reference numeral 91*a* shows an example in which the strip-like beam is applied onto the elements in the same line along the line of these elements, while reference numeral 91*b* shows an example in which the strip-like beam is applied onto the elements in such a way as to make an angle with respect to the direction of the line of the elements. In the example 91*a*, similarly to the case of the strip-like beam 61*a* shown in FIG. 6, the intensity (quantity) of a part of the beam detected by one element is roughly equal to the intensities of parts of the beam detected by other elements. On the other hand, in the case of the example 91*b*, the quantities of parts of the beam detected by the elements are different among the elements, and also in the elements other than the element 92, the strip-like beam is applied onto a plurality of elements. In such a beam application example 91*b*, the elements on a plurality of lines detect parts of the strip-like beam, and hence even if the quantity of part of the beam detected by the element 92 becomes the saturation state, the quantities of parts of the beams detected by other elements do not get to be saturated. For this reason, it is possible to increase the quantity of detected beam by increasing further the sensitivity for example, while it is also possible to suppress the increase in error. For this reason, the processing by the apparatus and the state of the apparatus can be detected with higher accuracy.

Figure 10:
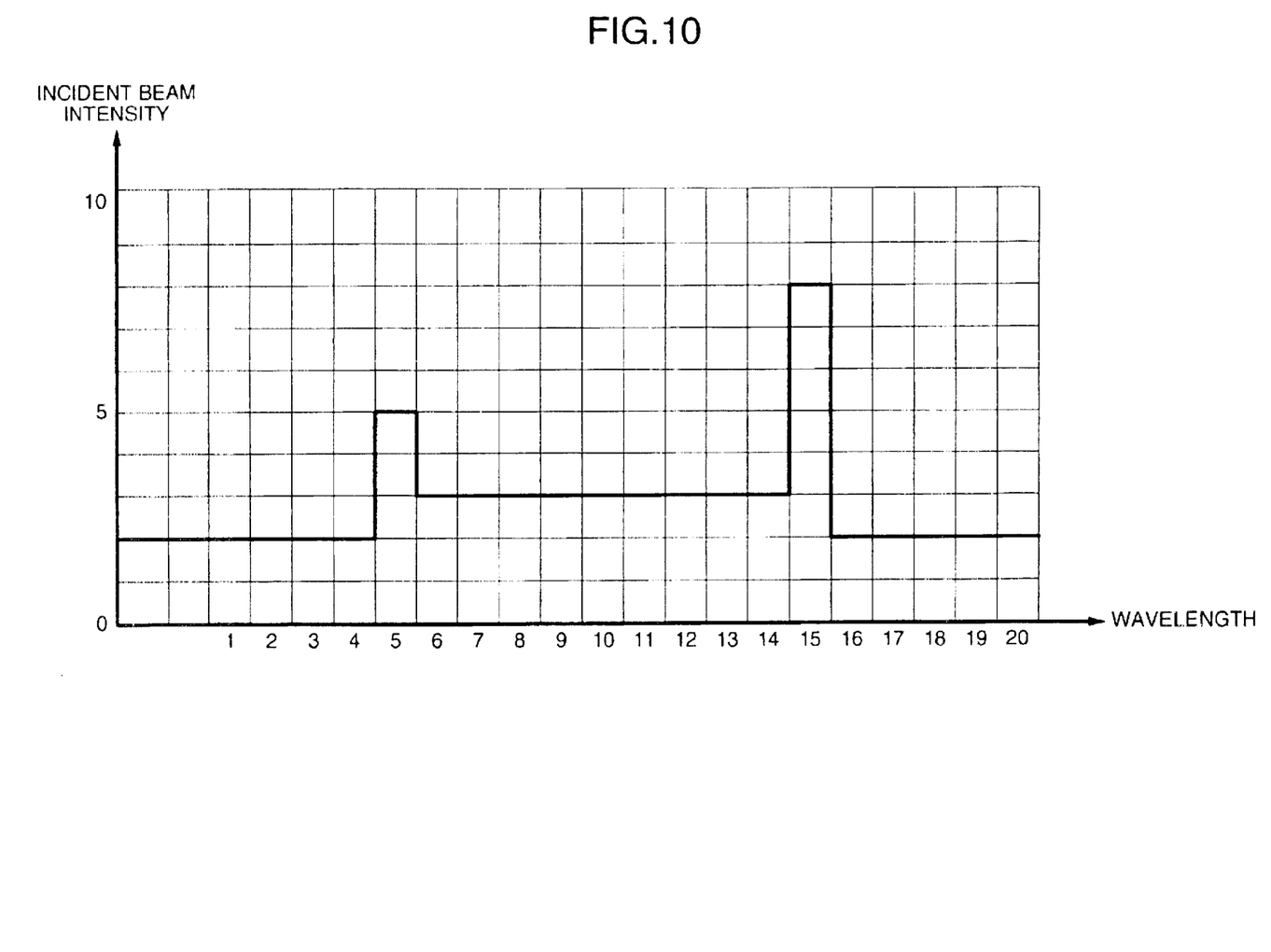
FIG. 10 is a graphical representation showing an example of spectra of the beams to be read out.

The description will now be given with respect to the processing of reading out the data of the spectra of the beams with reference to FIGS. 10 to 12. FIG. 10 shows an example of spectra of the beams to be read out. In the figure, the axis of abscissa represents the wavelength corresponding to the line (row) of the elements of the CCD, and the axis of ordinate represents the intensity of the incident beam. This figure corresponds to the spectra which are detected in the example of the beam application corresponding to the strip-like beam 61a shown in FIG. 6. In this example, the outputs having the intensities of 2 and 3 represent the offset voltages exhibiting the light from the background and the noises. In addition, as shown in the figure, a peak has the wavelength of 5.15 and the intensity of 5.8.

Figure 11:
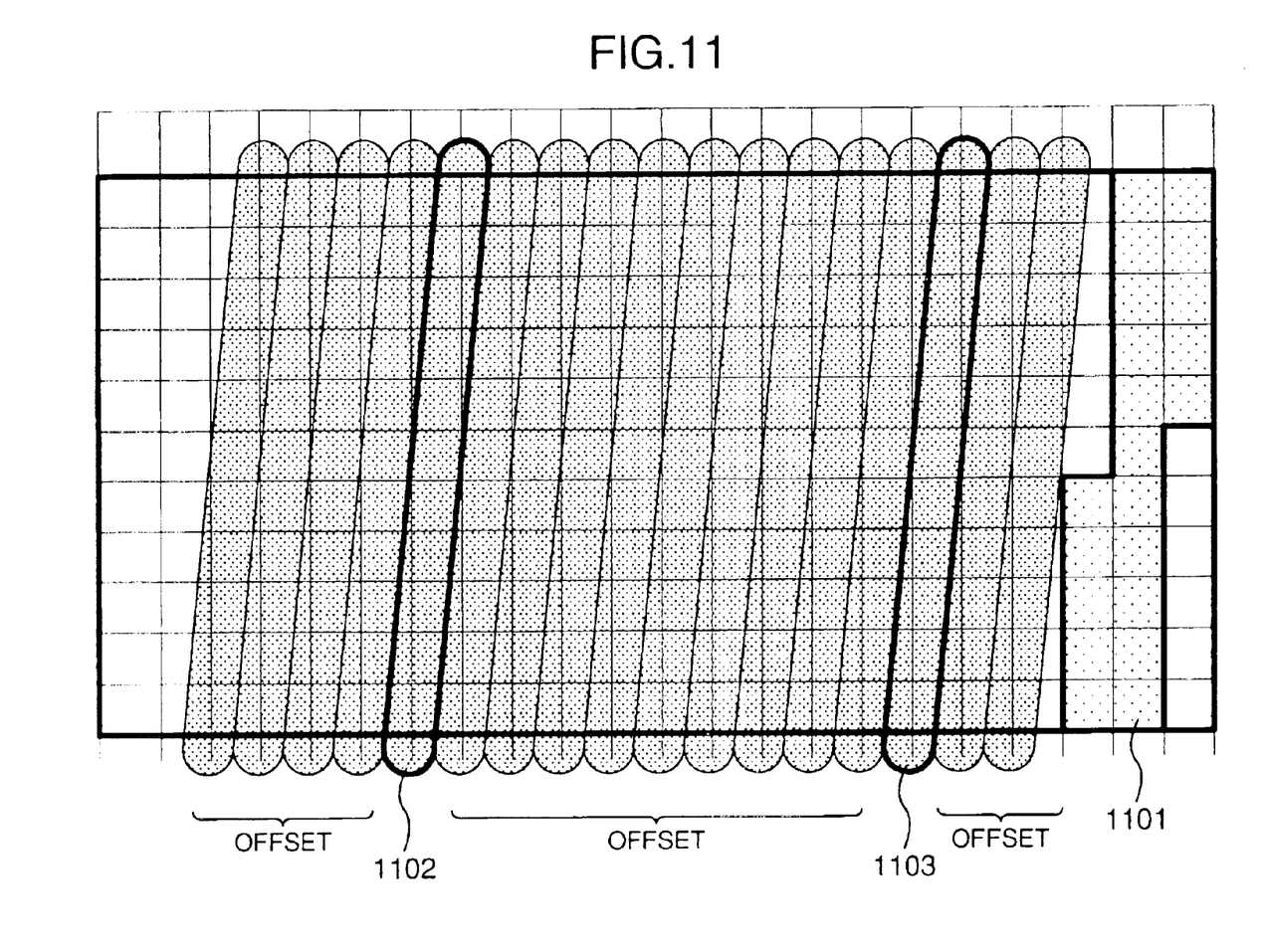
FIG. 11 is a schematic view showing the relationship between the application of the spectral strip-like beams and a read-out area.

FIG. 11 shows the relationship between the application of the spectral light beams and the readout areas. An area (window) 1101 of the elements of the sensor 24 for reading out the intensities of the beams (spectra) after the spectrum processing is shown within the solid frame in the right-hand end. Lines of the spectral strip-like beams each applied to the lines (in lengthwise and breadth directions on the drawing) of the elements in such a way as to make an angle with respect to each of the lines of the elements are shown on the left-hand side of the window 1101. The strip-like beams other than strip-like beams 1102 and 1103 are the incident beams corresponding to the above-mentioned offset voltages. In the read-out area 1101, the outputs of the elements in the areas are read out to be outputted. Then, in the present embodiment, the outputs of the elements in these areas are summed up to be outputted. In addition, in the present embodiment, the window 1101 is moved from the first colum of the elements to the 20-th column of the elements in the direction of the line (row) of the elements one column by one column. At this time, the beams are successively detected in the positions of the columns to output the optical output every column.

Figure 12:
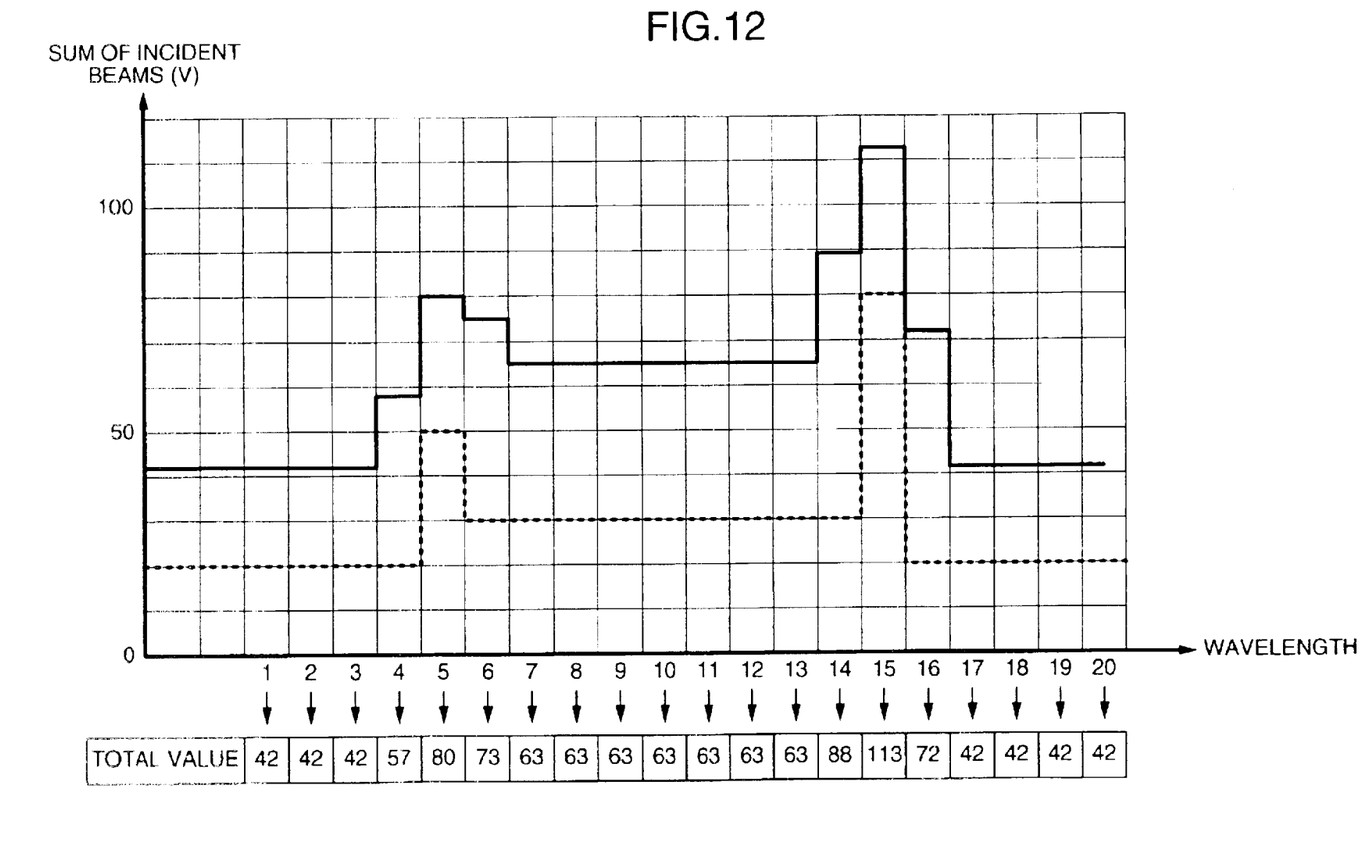
FIG. 12 is a graphical representation showing the result when the spectra shown in FIG. 10 are detected in the detection area according to the present embodiment.

FIG. 12 shows the result when the spectral strip-like light beams of FIG. 10 are detected in the detection areas in accordance with the present embodiment. A dotted line represents the outputs when the spectral strip-like beams shown in FIG. 10 are detected in the areas corresponding to the strip-like beam 61a as the reference example shown in FIG. 6. In addition, the total value of the outputs detected through the window shown in FIG. 11 is shown in the form of a numeric value below the graph. The numeric values below the axis of abscissa are the numeric values of the columns exhibiting the positions of the columns of the elements. Then, the numeric values are successively detected by moving the window one column by one column. In the figure, the spectra corresponding to the peaks are detected even in the positions before and after the positions 5 and 15 of the peaks. As a result, though the sharpness of the peak is reduced as compared with the case exhibited by the dotted line, it is understood that it is possible to detect the position of the peak and the value thereof.

As shown in the above-mentioned embodiment, each of the spectral strip-like beams is not applied along the single line of the elements, but is applied in such a way as to make an angle with respect to the line of the elements. For this reason, the quantities of parts of the beam applied to the different elements, in the same line, for detecting the wavelength of one spectral strip-like beam can be made different from one another. For this reason, even if the quantity of part of the beam detected by one element is saturated, the quantity (intensity) of part of the beam detected by the other element is still unsaturated, and hence it is possible to increase the quantity (the sensitivity or the detection time) of beams detected by the whole sensor. In addition, though the detection quantity is increased, the increase in error can be suppressed, and hence it is possible to enhance the accuracy of detection of the apparatus state.

In addition, the strip-like beam having one wavelength is applied over a plurality of lines of the areas each of which is adapted to detect the strip-like beam having one wavelength. For this reason, the detection quantity of beam can be made differ between the different lines of the areas. Therefore, even if the quantity of part of the beam detected by one element is saturated, the quantity (intensity) of part of the beam detected by another element is still unsaturated, and hence it is possible to increase the quantity (the sensitivity or the detection time) of beams detected by the whole sensor. In addition, though the detection quantity is increased, the increase in error can be suppressed, and hence it is possible to enhance the accuracy of detection of the apparatus state.

As described above, according to the present embodiment, it is possible to enhance the accuracy of the apparatus state such as the running condition of the apparatus, the state of the processing, or the judgement for the end point. Accordingly, the processing by the apparatus can be carried out with higher accuracy, the yield of the processing can be increased and the processing can be carried out with lower cost.

As set forth hereinabove, according to the present invention, it is possible to provide a plasma processing apparatus which is capable of carrying out the processing with higher accuracy.

It should be further understood by those skilled in the art that the foregoing description has been made on embodiments of the invention and that various changes and modifications may be made in the invention without departing from the spirit of the invention and the scope of the appended claims.

What is claimed is:

1. A plasma processing apparatus for processing an object arranged within a chamber by utilizing the plasma generated inside said chamber, said apparatus comprising:

a sensor having an array of a plurality of elements for detecting a plurality of strip-like beams, and having plural lines substantially in parallel along each of which a row of said plurality of elements is aligned;

an application device for applying the plurality of strip-like beams respectively having different wavelengths generated from the light within said chamber on the plural lines of said plurality of elements; and a controller adjusting the operation of said apparatus using outputs from said sensor, wherein directions of lines of said plurality of elements, for adjacent elements, are crossing, and said sensor detects one of said strip-like beams in a manner so that at least one of the plurality of the strip-like beams respectively having different wavelengths makes angles with respect to the direction of said plural lines, extending on at least portions of at least two adjacent ones of said plural lines.

2. A plasma processing apparatus according to claim 1, wherein the at least one of the plurality of the strip-like beams extends on at least portions of at least two adjacent ones of the plural lines of said elements so as to cross at least portions of the at least two adjacent ones of the plural lines of said elements.

3. A plasma processing apparatus comprising:

a sample stage, arranged within a chamber, for placing thereon an object to be processed utilizing a plasma generated within said chamber;

a spectroscope which introduces thereinto the light within said chamber through a slit to generate a plurality of beams having different wavelengths;

a sensor having an array of a plurality of elements, for detecting a plurality of strip-like beams, and having plural parallel lines alone each of which a row of said plurality of elements are aligned;

a detector which detects the intensities of the plurality of beams using outputs from said sensor; and a controller for adjusting the processing for the object to be processed using outputs from said detector;

wherein directions of lines of said plurality of elements, for adjacent elements, are crossing, and the plurality of strip-like beams respectively having different wavelengths are applied onto said elements in a manner so that at least one of the plurality of the strip-like beams respectively having different wavelengths makes angles with respect to the direction of the plural parallel lines, extending on at least portions of at least two adjacent ones of said plural parallel lines.

4. A plasma processing apparatus according to claim 3, wherein the at least one of the plurality of the strip-like beams extends on at least portions of at least two adjacent ones of the plural parallel lines so as to cross at least portions of the at least two adjacent ones of the plural parallel lines.

* * * * *